US012734373B2

(12) United States Patent
Fujii

(10) Patent No.: US 12,734,373 B2
(45) Date of Patent: Sep. 15, 2026

(54) RADIOTHERAPY DEVICE COMPRISING A POSITIONING DEVICE, AND POSITIONING METHOD

(71) Applicant: Hitachi High-Tech Corporation, Tokyo (JP)

(72) Inventor: Takaaki Fujii, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 88 days.

(21) Appl. No.: 18/689,116

(22) PCT Filed: Aug. 12, 2022

(86) PCT No.: PCT/JP2022/030807
§ 371 (c)(1),
(2) Date: Mar. 5, 2024

(87) PCT Pub. No.: WO2023/079811
PCT Pub. Date: May 11, 2023

(65) Prior Publication Data

US 2024/0366963 A1 Nov. 7, 2024

(30) Foreign Application Priority Data

Nov. 8, 2021 (JP) ................................ 2021-181771

(51) Int. Cl.
*A61N 5/10* (2006.01)

(52) U.S. Cl.
CPC ............ *A61N 5/1049* (2013.01); *A61N 5/10* (2013.01); *A61N 5/1048* (2013.01);
(Continued)

(58) Field of Classification Search
CPC ........ A61N 5/10; A61N 5/103; A61N 5/1031; A61N 5/1037; A61N 5/1042;
(Continued)

(56) References Cited

U.S. PATENT DOCUMENTS 6,516,046 B1 2/2003 Frohlich et al.
6,865,253 B2 * 3/2005 Blumhofer ........... A61N 5/1049 378/65

(Continued)

FOREIGN PATENT DOCUMENTS

JP 2013-099431 A 5/2013
JP 2017-189285 A 10/2017

(Continued)

OTHER PUBLICATIONS

International Search Report of PCT/JP2022/030807 dated Oct. 25, 2022.

(Continued)

*Primary Examiner* — Allen C. Ho
(74) *Attorney, Agent, or Firm* — MATTINGLY & MALUR, PC

(57) ABSTRACT

A positioning device, a radiotherapy device, and a positioning method enable accurate patient positioning while reducing calculation time. A plurality of X-ray fluoroscopic images are obtained by imaging a patient along each of a plurality of imaging axes in a direction different from a plurality of movement axes along which a treatment couch moves translationally. A plurality of simulated-X-ray fluoroscopic images are obtained by projecting the three-dimensional fluoroscopic image of the patient on each of the plurality of surfaces corresponding to each imaging axis. A similarity calculation unit calculates the similarity between each X-ray fluoroscopic image and each simulated-X-ray fluoroscopic image. Based on the similarity, an optimization calculation processing unit calculates the movement amount of the treatment couch such that each X-ray fluoroscopic image and each simulated-X-ray fluoroscopic image coincide most in each of the plurality of translation directions along each of the plurality of optimization axes.

7 Claims, 5 Drawing Sheets

(52) U.S. Cl.
CPC .... *A61N 5/1081* (2013.01); *A61N 2005/1056* (2013.01); *A61N 2005/1061* (2013.01); *A61N 2005/1074* (2013.01); *A61N 2005/1087* (2013.01)

(58) Field of Classification Search
CPC ................ A61N 5/1048; A61N 5/1049; A61N 2005/1061; A61N 2005/1062; A61N 5/1064; A61N 5/1065; A61N 5/1067; A61N 5/1068; A61N 5/1069; A61N 5/107; A61N 5/1071; A61N 2005/1072; A61N 2005/1074; A61N 5/1077; A61N 5/1081; A61N 2005/1087
USPC .............................. 250/492.1, 492.3; 378/65
See application file for complete search history.

(56) References Cited

U.S. PATENT DOCUMENTS 6,990,175 B2 * 1/2006 Nakashima .......... A61N 5/1049 378/92
7,412,086 B2 * 8/2008 Sakas .................. A61N 5/1049 378/65
7,522,779 B2 * 4/2009 Fu ........................ A61N 5/1049 382/167
7,609,810 B2 * 10/2009 Yi ........................ A61N 5/1049 378/65
7,620,144 B2 * 11/2009 Bodduluri ............ A61N 5/1049 378/65
7,623,623 B2 * 11/2009 Raanes ................ A61N 5/1049 378/68
7,672,429 B2 * 3/2010 Urano .................. A61N 5/1049 378/65
7,831,073 B2 * 11/2010 Fu ........................ A61N 5/1049 382/128
7,894,649 B2 * 2/2011 Fu ........................ A61N 5/1049 378/65
8,086,004 B2 * 12/2011 Kuduvalli ............ A61N 5/1075 382/128
8,457,372 B2 * 6/2013 Fu ........................ A61N 5/1049 382/128
8,471,222 B2 * 6/2013 Handa .................. A61N 5/1069 378/65
8,559,596 B2 * 10/2013 Thomson ............. A61N 5/1049 378/65
8,761,863 B2 * 6/2014 Ishikawa .............. A61N 5/1049 600/1
8,824,630 B2 * 9/2014 Maurer, Jr. .......... A61N 5/1077 378/68
9,108,048 B2 * 8/2015 Maurer, Jr. .......... A61N 5/1049
9,616,251 B2 * 4/2017 Filiberti ............... A61N 5/1075
9,724,049 B2 * 8/2017 Umekawa ............ A61N 5/1049
10,016,625 B2 * 7/2018 Taguchi ............... A61N 5/1049
10,625,099 B2 * 4/2020 Takahashi ............ A61N 5/1049
10,722,733 B2 * 7/2020 Takahashi ............ A61N 5/1049
10,737,117 B2 * 8/2020 Mori .................... A61N 5/1065
10,835,762 B2 * 11/2020 Mori .................... A61N 5/1067
10,940,331 B2 * 3/2021 Mori .................... A61N 5/1064
10,952,695 B2 * 3/2021 Mori .................... A61N 5/1049
11,049,252 B2 * 6/2021 Miyazaki ............. A61N 5/1049
11,141,126 B2 * 10/2021 Mori .................... A61N 5/1037
11,282,244 B2 * 3/2022 Umekawa ............ A61N 5/1049
11,446,520 B2 * 9/2022 Fujii .................... A61N 5/1048
11,478,662 B2 * 10/2022 Sayeh .................. A61N 5/1049
11,596,807 B2 * 3/2023 Maurer ................ A61N 5/1037
11,660,471 B2 * 5/2023 Miyazaki ............. A61N 5/1077 600/1
11,712,582 B2 * 8/2023 Miyazaki ............. A61N 5/1049 378/65
11,830,184 B2 * 11/2023 Hirai ...................... A61N 5/103
12,059,579 B2 * 8/2024 Karasawa ............ A61N 5/1049
12,128,252 B2 * 10/2024 Jordan ................. A61N 5/1045
12,165,321 B2 * 12/2024 Sakata ..................... A61N 5/10
12,364,877 B2 * 7/2025 Hirai .................... A61N 5/1049
2002/0085668 A1 7/2002 Blumhofer et al.
2006/0058620 A1 3/2006 Sakas et al.
2017/0291042 A1 10/2017 Takahashi

FOREIGN PATENT DOCUMENTS

JP 6668902 B2 3/2020
WO 2018/225234 A1 12/2018

OTHER PUBLICATIONS

Extended European Search Report received in corresponding European Application No. 22889636.1 dated Aug. 22, 2025.
Communication Pursuant to Article 94(3) EPC received in corresponding European Application No. 22 889 636.1 dated Jul. 13, 2026.

* cited by examiner

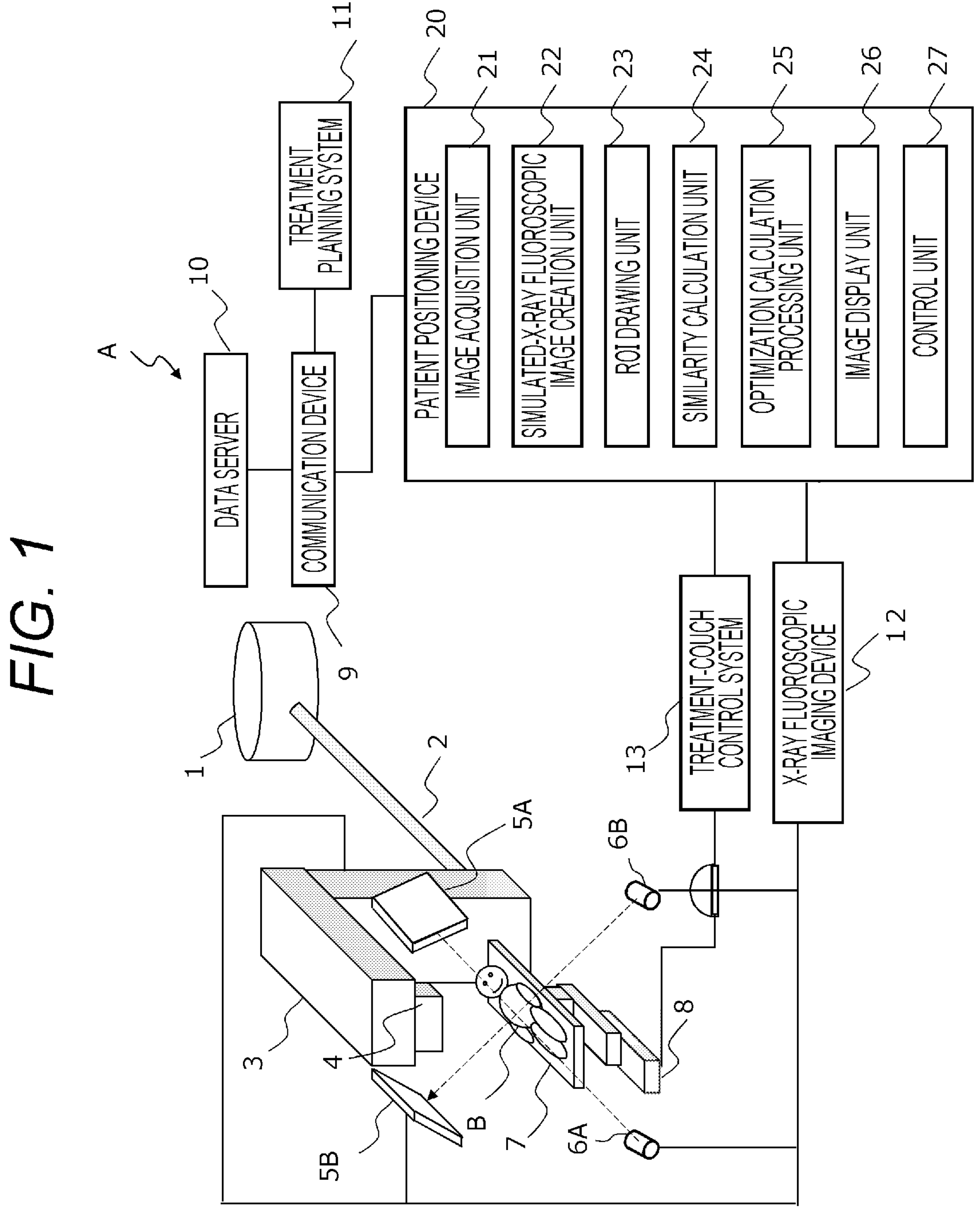
FIG. 1
A
10
DATA SERVER
COMMUNICATION DEVICE
9
TREATMENT PLANNING SYSTEM
11
20
PATIENT POSITIONING DEVICE
21
IMAGE ACQUISITION UNIT
22
SIMULATED-X-RAY FLUOROSCOPIC IMAGE CREATION UNIT
23
ROI DRAWING UNIT
24
SIMILARITY CALCULATION UNIT
25
OPTIMIZATION CALCULATION PROCESSING UNIT
26
IMAGE DISPLAY UNIT
27
CONTROL UNIT
13
TREATMENT-COUCH CONTROL SYSTEM
12
X-RAY FLUOROSCOPIC IMAGING DEVICE
1
2
3
4
5A
5B
6A
6B
7
8
B

RADIOTHERAPY DEVICE COMPRISING A POSITIONING DEVICE, AND POSITIONING METHOD

TECHNICAL FIELD

The present disclosure relates to a positioning device, a radiotherapy device, and a positioning method.

BACKGROUND ART

As one of cancer treatment methods, radiotherapy for irradiating a patient with radiation is known. Radiation used in radiotherapy is roughly classified into an uncharged particle beam such as an X-ray or a gamma ray and a charged particle beam such as a proton beam or a carbon ion beam. Radiotherapy using the latter charged particle beam is generally called particle beam therapy.

In the case of the uncharged particle beam, a dose decreases at a constant rate from a shallow position to a deep position in a body. Meanwhile, in the case of the charged particle beam, a dose distribution (black curve) having a peak of energy loss at a specific depth can be formed. Therefore, by matching the peak of the energy loss of the charged particle beam with a position of a tumor, it is possible to greatly reduce the dose of the charged particle beam with which normal tissue at a position deeper than the tumor is irradiated.

For this reason, in the radiotherapy, it is important to accurately irradiate a target tumor with a desired dose of radiation for improving the therapeutic effect. In order to accurately irradiate the tumor with radiation, it is necessary to align the position of the patient at the same position as a planned position determined by the treatment planning created in advance. This alignment of the patient is called patient positioning.

As a method of positioning a patient in radiotherapy, there is a method using X-ray fluoroscopic images (Digital Radiography: DR) obtained by imaging a patient lying on a treatment couch from two different directions by two sets of X-ray tubes and a flat panel detector (FPD). In this method, the X-ray fluoroscopic image obtained by imaging a patient at the time of radiotherapy is compared with a simulated-X-ray fluoroscopic image created from a computed tomography (CT) image used for creating a treatment planning, and positioning of the patient is performed such that the position of a positioning target structure such as a bone matches between the X-ray fluoroscopic image and the simulated-X-ray fluoroscopic image.

In general, the X-ray fluoroscopic image may include a structure other than the positioning target structure, such as a fixing tool and a soft tissue of a patient, or the arrangement of a bone, which is the positioning target structure, may change from the time of treatment planning. In such a situation, the structures captured in the X-ray fluoroscopic image and the simulated-X-ray fluoroscopic image do not match over the entire image. In this case, the patient is positioned using a region of interest (ROI) set as a region where the positioning target structure exists on the X-ray fluoroscopic image. Note that the setting of the region of interest is usually performed by a user who is a medical worker drawing the region of interest on an image.

The automatic positioning for positioning the patient is performed by using a translation amount and a rotation amount of a treatment couch on which the patient is sleeping as parameters and calculating an optimum value of the parameters by optimization calculation. Normally, the translation amount has three components along three axes (x, y, z) orthogonal to each other, and the rotation amount has three components (Pitch, Roll, Yaw) with the three axes as rotation axes. Therefore, in the optimization calculation, an optimization process for each of the six components is repeatedly performed to calculate the optimum value of the parameter. In addition, defining the translation amount coincide with a movement axis of the treatment couch for arranging the patient at a planned position, the x axis is oriented in a direction from right to left (Right-Left direction: RL direction) as viewed from the patient lying on the treatment couch on his back, the y axis is oriented in a direction from the foot to the head (Superior-Inferior direction: SI direction), and the z axis is oriented in a direction from the back to the abdomen (Anterior-Posterior: AP direction).

However, in a case where the axis of the parameter on which the optimization calculation is performed is different from an imaging axis of an imaging device, the optimum value of the parameter may not be reached in the optimization calculation, or the calculation amount in the optimization calculation may increase.

Meanwhile, PTLs 1 and 2 disclose a technique for reducing the number of calculations for repeating the optimization process in the optimization calculation by adding an optimization process in a one-dimensional direction with respect to a direction along an imaging axis for capturing the X-ray fluoroscopic image after the optimization process for each component is completed in the optimization calculation.

In addition, PTL 3 discloses a technique of reducing the number of X-ray fluoroscopic images by evaluating the optimization of the translation amount with respect to the direction along the imaging axis only in one direction orthogonal to the fluoroscopic imaging thereby reducing the time required for positioning the patient.

CITATION LIST

Patent Literature

PTL 1: Japanese Patent No. 6668902
PTL 2: WO 2018/225234 A
PTL 3: JP 2013-99431 A

SUMMARY OF INVENTION

Technical Problem

In the techniques disclosed in PTLs 1 and 2, since an optimization process for a direction along an imaging axis is added after an optimization process for a normal multidimensional component is completed, there is a problem that a reduction rate of calculation time is low because the optimization process per calculation increases.

In addition, the technique disclosed in PTL 3 has a problem that it is difficult to calculate an optimum value of the parameter depending on the position of the region of interest on the image. For example, in a case where a small region of interest is set at an end of an image, when the translation amount with respect to a direction along a certain imaging axis is changed, on an image acquired by another imaging axis orthogonal to the imaging axis, the positioning target structure in the region of interest may move to the end or center portion of the image and move out of the region of interest. In this case, it is difficult to calculate the optimum value.

An object of the present disclosure is to provide a positioning device, a radiotherapy device, and a positioning method that enable highly accurate patient positioning while further reducing calculation time.

Solution to Problem

According to one aspect of the present disclosure, there is provided a positioning device that controls a position of a treatment couch on which a subject is mounted, the positioning device including: an image acquisition unit that acquires a plurality of fluoroscopic images obtained by imaging the subject along each of a plurality of imaging axes in a direction different from a plurality of movement axes along which the treatment couch translationally moves; a creation unit that creates a plurality of simulated fluoroscopic images obtained by projecting a three-dimensional fluoroscopic image of the subject onto each of a plurality of surfaces corresponding to each imaging axis; a calculation unit that calculates similarity between each of the fluoroscopic images and each of the simulated fluoroscopic images; and an optimization unit that calculates, based on the similarity, a movement amount of the treatment couch such that each fluoroscopic image and each simulated fluoroscopic image match most in each of a plurality of translation directions along each of a plurality of optimization axes including the plurality of imaging axes and a plurality of rotation directions around a plurality of rotation axes.

Advantageous Effects of Invention

According to the present invention, highly accurate patient positioning is possible while further reducing the calculation time.

BRIEF DESCRIPTION OF DRAWINGS

FIG. 1 is a diagram illustrating an overall configuration of a particle beam therapy system according to one embodiment of the present disclosure.

DESCRIPTION OF EMBODIMENTS

Figure 2:
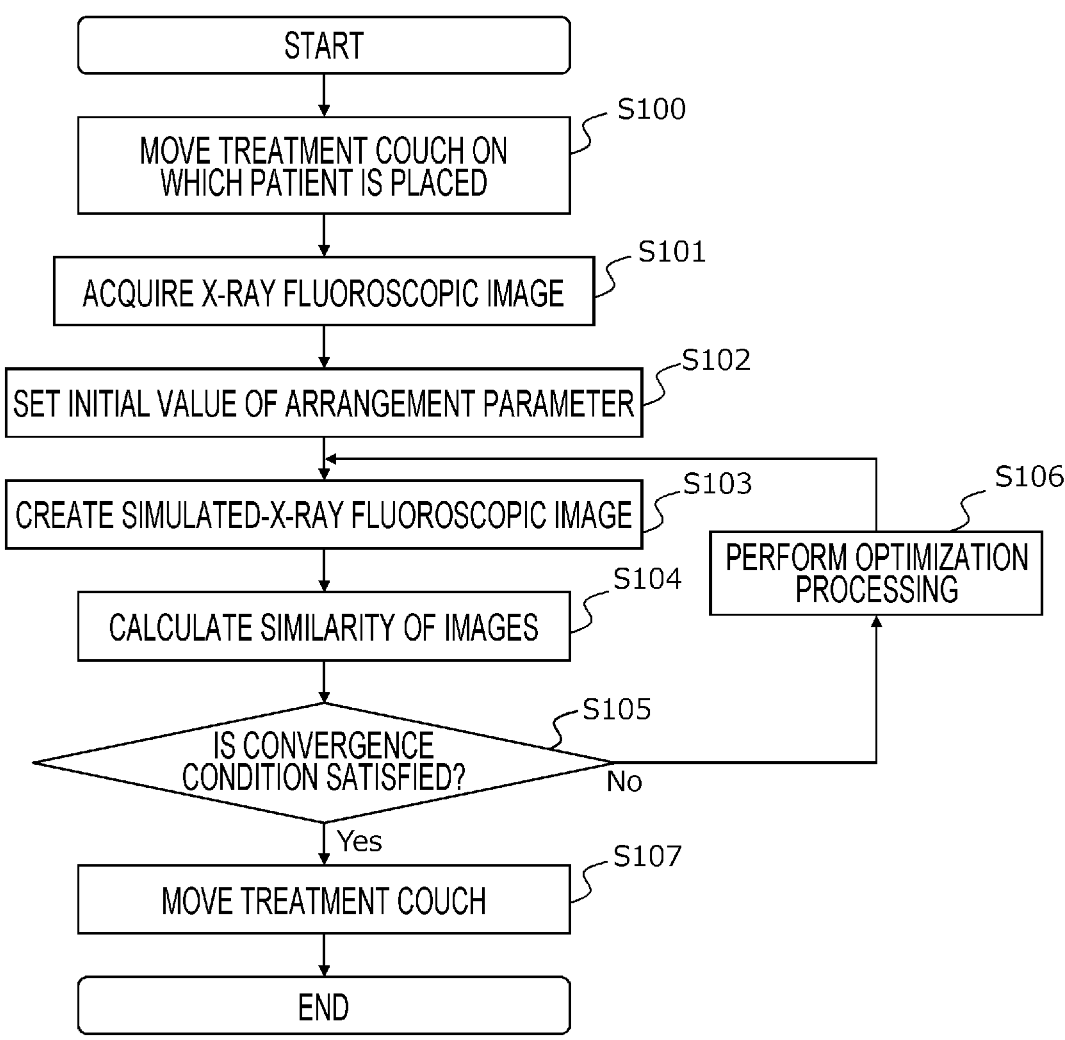
FIG. 2 is a flowchart for explaining an example of patient positioning processing.

Hereinafter, embodiments of the present disclosure will be described with reference to the drawings.

Note that the following description and drawings are examples for describing the present invention, and omission and simplification are appropriately made for clarity of description. The present invention can be implemented in various other forms. Unless otherwise specified, each component may be singular or plural. In the drawings for describing the embodiments, the same reference numerals are given to portions having the same functions, and repeated description thereof may be omitted. In addition, the position, size, shape, range, and the like of each component illustrated in the drawings may not represent the actual position, size, shape, range, and the like in order to facilitate understanding of the invention. Therefore, the present invention is not limited to the position, size, shape, range, and the like disclosed in the drawings. In addition, in a case where there are a plurality of the same or similar constituent elements, there is a case where description is given with different subscripts attached to the same reference numerals. However, in a case where it is not necessary to distinguish the plurality of components, the description may be made while omitting the subscript.

FIG. 1 is a diagram illustrating an overall configuration of a particle beam therapy system according to one embodiment of the present disclosure. A particle beam therapy system A illustrated in FIG. 1 is a radiotherapy device having a group of apparatuses for irradiating a patient B who is a subject with a particle beam as a target. The particle beam therapy system A includes an accelerator 1, a beam transport device 2, a gantry 3, an irradiation nozzle 4, FPDs 5A and 5B, X-ray tubes 6A and 6B, a treatment couch 7, a robot arm 8, a communication device 9, a data server 10, a treatment planning system 11, a X-ray fluoroscopic imaging device 12, a treatment-couch control system 13, and a patient positioning device 20.

The accelerator 1 is a particle beam generator that generates a particle beam to be emitted to the patient B, and accelerates and outputs the particle beam until the particle beam has energy suitable for treatment of the patient B. The beam transport device 2 transports the particle beam output from the accelerator 1 to the gantry 3. The type of the particle beam is not particularly limited, and is, for example, a proton beam or a carbon ion beam.

The gantry 3 and the irradiation nozzle 4 are irradiation devices that irradiate the patient B with the particle beam transported from the accelerator 1. The gantry 3 adjusts an irradiation angle at which the patient B is irradiated with the particle beam transported from the accelerator 1. Specifically, the gantry 3 has a rotation mechanism capable of surrounding the patient B and rotating by 360°, and adjusts the irradiation angle by rotating. The irradiation nozzle 4 is provided in the gantry 3, and irradiates the patient B with the particle beam transported to the gantry 3. A mechanism for adjusting the shape of the particle beam to match a target shape of the patient may be incorporated in the irradiation nozzle 4.

The FPDs 5A and 5B and the X-ray tubes 6A and 6B constitute an imaging system that performs fluoroscopic imaging of the patient B. The FPDs 5A and 5B are planar detectors that detect X-rays and images the patient B. The X-ray tubes 6A and 6B output X-rays. The FPD 5A and the X-ray tube 6A are arranged to face each other such that the X-ray output from the X-ray tube 6A is detected by the FPD 5A, and the FPD 5B and the X-ray tube 6B are arranged to face each other such that the X-ray output from the X-ray tube 6B is detected by the FPD 5B. An axis connecting the center of the FPD 5A and the X-ray tube 6A and an axis connecting the center of the FPD 5B and the X-ray tube 6B are two imaging axes for imaging the patient. The two imaging axes are preferably orthogonal to each other, but may not be orthogonal to each other. The particle beam therapy system A may include three or more FPDs and three or more X-ray tubes. In this case, the number of imaging axes is also three or more.

The treatment couch 7 is a table on which the patient B is placed when the patient B is irradiated with the particle beam. The robot arm 8 is a device that moves the treatment couch 7. Specifically, the robot arm 8 performs translational movement in a plurality of translational directions along each of a plurality of movement axes and rotational movement in a plurality of rotational directions about a plurality of rotation axes with respect to the treatment couch 7. In the present embodiment, the rotation axis is the same as the movement axis, and there are three movement axes (rotation axes). In addition, each movement axis is directed in a direction from right to left (RL direction) as viewed from the patient B lying on the treatment couch 7 on his back, a direction from the foot to the head (SI direction) of the patient B, and a direction from the back to the abdomen (AP direction).

The communication device 9 communicably connects the data server 10, the treatment planning system 11, and the patient positioning device 20 to each other.

The data server 10 is a storage device that stores various types of information regarding the particle beam therapy of the patient B. The data server 10 stores, for example, three-dimensional fluoroscopic image information of the patient B and treatment planning information indicating a treatment planning of the patient B. The three-dimensional fluoroscopic image includes information indicating the shape and electron density of the patient in units of voxels. The three-dimensional fluoroscopic image is, for example, a computed tomography (CT) imaging image, and is generated in advance (before creating treatment planning information of the patient B). The treatment planning information is generated based on the three-dimensional fluoroscopic image. In addition, the treatment planning information includes plan arrangement information indicating planned arrangement that is arrangement of the patient B at the time of treatment. The arrangement of the patient B indicates the position and angle (posture) of the patient B, and is determined by the position and angle of the treatment couch 7.

The treatment planning system 11 creates the treatment planning for the patient B based on the three-dimensional fluoroscopic image information stored in the data server 10, and stores treatment planning information indicating the treatment planning in the data server 10.

The X-ray fluoroscopic imaging device 12 controls each of the FPD 5A and the X-ray tube 6A, and the FPD 5B and the X-ray tube 6B to acquire a plurality of X-ray fluoroscopic images obtained by capturing the patient B from different angles, and transmits the acquired X-ray fluoroscopic images to the positioning device 20. In the present embodiment, there are two X-ray fluoroscopic images.

The treatment-couch control system 13 adjusts the arrangement of the patient B by controlling the robot arm 8 to adjust the arrangement of the treatment couch 7.

The patient positioning device 20 executes positioning processing of the patient B based on the three-dimensional fluoroscopic image information and the treatment planning information stored in the data server 10 and the X-ray fluoroscopic acquired by the X-ray fluoroscopic imaging device 12.

The positioning processing of the patient B is processing of arranging the patient B placed on the treatment couch 7 in the same arrangement as the planned arrangement indicated by the treatment planning information before starting the particle beam therapy of the patient B. The patient positioning device 20 controls the robot arm 8 via the treatment-couch control system 13 to adjust the position and angle of the treatment couch 7, thereby arranging the patient B in the same arrangement as the planned arrangement.

When the positioning processing is completed, the particle beam therapy of the patient B is actually performed. Specifically, the particle beam accelerated to energy suitable for treatment by the accelerator 1 is transported to the gantry 3 via the beam transport device 2. The particle beam is deflected in an appropriate direction by the gantry 3, passes through the irradiation nozzle 4, and is irradiated to the target volume of the patient B.

Hereinafter, the positioning device 20 will be described in more detail.

As illustrated in FIG. 1, the positioning device 20 includes an image acquisition unit 21, a simulated-X-ray fluoroscopic image creation unit 22, an ROI drawing unit 23, a similarity calculation unit 24, an optimization calculation processing unit 25, an image display unit 26, and a control unit 27.

The image acquisition unit 21 acquires three-dimensional fluoroscopic image information from the data server 10 via the communication device 9, and acquires a X-ray fluoroscopic image from the X-ray fluoroscopic imaging device 12.

The simulated-X-ray fluoroscopic image creation unit 22 is a creation unit that creates a plurality of simulated-X-ray fluoroscopic images which are a plurality of simulated fluoroscopic images obtained by projecting the three-dimensional fluoroscopic image acquired by the image acquisition unit 21 onto each of a plurality of surfaces corresponding to each imaging axis for capturing the X-ray fluoroscopic image. The simulated-X-ray fluoroscopic image creation unit 22 creates the simulated-X-ray fluoroscopic image by arranging the three-dimensional image of the patient B on the same virtual space as the imaging system that has generated the X-ray fluoroscopic image and performing projection processing. The surface corresponding to the imaging axis is, for example, a surface orthogonal to the imaging axis.

The ROI drawing unit 23 specifies an ROI which is a region of interest used for positioning the patient in the simulated-X-ray fluoroscopic image. Specifically, the ROI drawing unit 23 displays the simulated-X-ray fluoroscopic image and causes the user to draw the ROI on the simulated-X-ray fluoroscopic image to specify the ROI. The ROI is drawn to include, for example, a positioning target structure such as a bone.

The similarity calculation unit 24 calculates the similarity between the X-ray fluoroscopic image and the simulated-X-ray fluoroscopic image in the ROI specified by the ROI drawing unit 23. In the present embodiment, the similarity calculation unit 24 calculates a total value of the similarity between the X-ray fluoroscopic image and the simulated-X-ray fluoroscopic image corresponding to each of the two imaging axes.

The similarity is not particularly limited as long as it is an index capable of evaluating the similarity of images, and is, for example, a mutual information or a normalized cross correlation (Zero-mean Normalized Cross Correlation: ZNCC). The normalized cross correlation $S_{ZNCC}$ is calculated by Formula (1).

[Mathematical Formula 1]

$$S_{ZNCC} = \frac{\sum_{i=1}^{n}\sum_{j=1}^{m}\{(g(i,j)-\mu_g)(f(i,j)-\mu_f)\}}{\sqrt{\sum_{i=1}^{n}\sum_{j=1}^{m}(g(i,j)-\mu_g)^2}\sqrt{\sum_{i=1}^{n}\sum_{j=1}^{m}(f(i,j)-\mu_f)^2}} \qquad (1)$$

Here, g (i, j) is a pixel value of a pixel (i, j) of the X-ray fluoroscopic image, f (i, j) is a pixel value of a pixel (i, j) of the simulated-X-ray fluoroscopic image, $\mu_g$ is an average intensity of the X-ray fluoroscopic image, and $\mu_f$ is an average intensity of the simulated-X-ray fluoroscopic image.

The optimization calculation processing unit 25 is an optimization unit that calculates the movement amount of the treatment couch 7 such that the X-ray fluoroscopic image and the simulated-X-ray fluoroscopic image match most in the ROI specified by the ROI drawing unit 23 based on the similarity calculated by the similarity calculation unit 24. Specifically, the optimization calculation processing unit 25 calculates the movement amount of the treatment couch 7 by optimizing the values of the arrangement parameters corresponding to the movement amounts of the translational movement and the rotational movement of the treatment couch 7 using a predetermined optimization calculation method. The arrangement parameters have three degrees of freedom for translational movement and three degrees of freedom for rotational movement. The optimization calculation method is not particularly limited, and is, for example, a Broyden-Fletcher-Goldfarb-Shanno (BFGS) method, a Nelder-Mead method, a Powell method, or the like belonging to the quasi-Newton method.

The image display unit 26 is a display unit that displays various types of information and images. For example, the image display unit 26 displays the X-ray fluoroscopic image, the simulated-X-ray fluoroscopic image, the ROI image indicating the ROI region, and the like.

The control unit 27 controls the treatment-couch control system 13 to adjust the arrangement of the treatment couch 7, thereby adjusting the arrangement of the patient B.

The positioning device 20 having the above functions can be realized by an information processing device capable of performing various types of information processing such as a computer device. The information processing device includes, for example, an arithmetic element, a storage medium, and a communication interface, and further includes an input unit such as a mouse and a keyboard, and a display unit such as a display as necessary.

The arithmetic element is, for example, a processor such as a central processing unit (CPU) and a field-programmable gate array (FPGA). Examples of the storage medium include a magnetic storage medium such as a hard disk drive (HDD), and a semiconductor storage medium such as a random access memory (RAM), a read only memory (ROM), and a solid state drive (SSD). In addition, a combination of an optical disk such as a digital versatile disk (DVD) and an optical disk drive may be used as the storage medium. Furthermore, another high-value storage medium such as a magnetic tape medium may be used as the storage medium.

A program such as firmware is stored in the storage medium. When the operation of the positioning device 20 is started (for example, when the power supply is turned on), the arithmetic element reads the program from the storage medium and executes the program, whereby each of the units 21 to 27 of the positioning device 20 is realized, and a series of overall control is executed. Furthermore, in addition to the program, data and the like necessary for each processing of the positioning device 20 are stored in the storage medium.

Note that the positioning device 20 of the present embodiment may be configured by so-called cloud computing in which a plurality of information processing devices can communicate via a communication network.

Hereinafter, the patient positioning processing by the patient positioning device 20 will be described in more detail with reference to FIGS. 2 to 6.

FIG. 2 is a flowchart for explaining an example of the patient positioning processing.

It is assumed that the patient B is disposed in a setup position of the treatment couch 7. The setup position is a position for arranging the patient B in the same arrangement as the planned arrangement. For example, a position of a body surface of the patient B on the treatment couch 7 is measured using an infrared laser installed in the treatment room, and the patient B is arranged in the setup position of the treatment couch 7 based on the position.

In the patient positioning processing, first, the control unit 27 acquires the treatment planning information from the data server 10, and controls the robot arm 8 via the treatment-couch control system 13 based on the plan arrangement information included in the treatment planning information to move the treatment couch 7 on which the patient B is placed such that the arrangement of the patient B is the planned arrangement indicated by the plan arrangement information (Step S100). In this case, the positioning target structure of the patient B placed on the treatment couch 7 is included in the X-ray irradiation region formed by the FPDs 5A and 5B and the X-ray tubes 6A and 6B.

Thereafter, the image acquisition unit 21 acquires a plurality of pieces of X-ray fluoroscopic image information obtained by imaging the patient B from a plurality of different directions via the X-ray fluoroscopic imaging device 12 (Step S101). In the present embodiment, the image acquisition unit 21 acquires two pieces of X-ray fluoroscopic image information imaged from two directions along two imaging axes.

The simulated-X-ray fluoroscopic image creation unit 22 acquires the three-dimensional fluoroscopic image information from the data server 10, and sets an initial value of a displacement amount of the arrangement parameter based on the three-dimensional fluoroscopic image information (Step S102). For example, the simulated-X-ray fluoroscopic image creation unit 22 displays the three-dimensional fluoroscopic image information on the image display unit 26, and causes the user to input the initial value. Note that the simulated-X-ray fluoroscopic image creation unit 22 may set a predetermined value as the initial value without the user.

The simulated-X-ray fluoroscopic image creation unit 22 creates two simulated-X-ray fluoroscopic images by projecting the three-dimensional fluoroscopic image information on the plane assuming the same imaging system as the imaging system of the X-ray fluoroscopic image information (Step S103).

The ROI drawing unit 23 displays the simulated-X-ray fluoroscopic image information and specifies the ROI drawn by the user. The similarity calculation unit 24 calculates the similarity between the X-ray fluoroscopic image information and the simulated-X-ray fluoroscopic image information in the ROI (Step S104).

The optimization calculation processing unit 25 determines whether or not the similarity satisfies a preset convergence condition (Step S105).

When the similarity does not satisfy the convergence condition (Step S105: No), the optimization calculation processing unit 25 optimizes the arrangement parameters by performing optimization processing for adjusting the arrangement parameters (Step S106).

Meanwhile, when the similarity satisfies the convergence condition (Step S105: Yes), the control unit 27 moves the treatment couch 7 via the treatment-couch control system 13 based on the adjusted arrangement parameter (Step S107), and ends the patient positioning processing. This makes it possible to move the patient from the current arrangement to the arrangement at the time of treatment planning and perform the positioning precisely. Thereafter, irradiation with an actual particle beam is performed.

Figure 3:
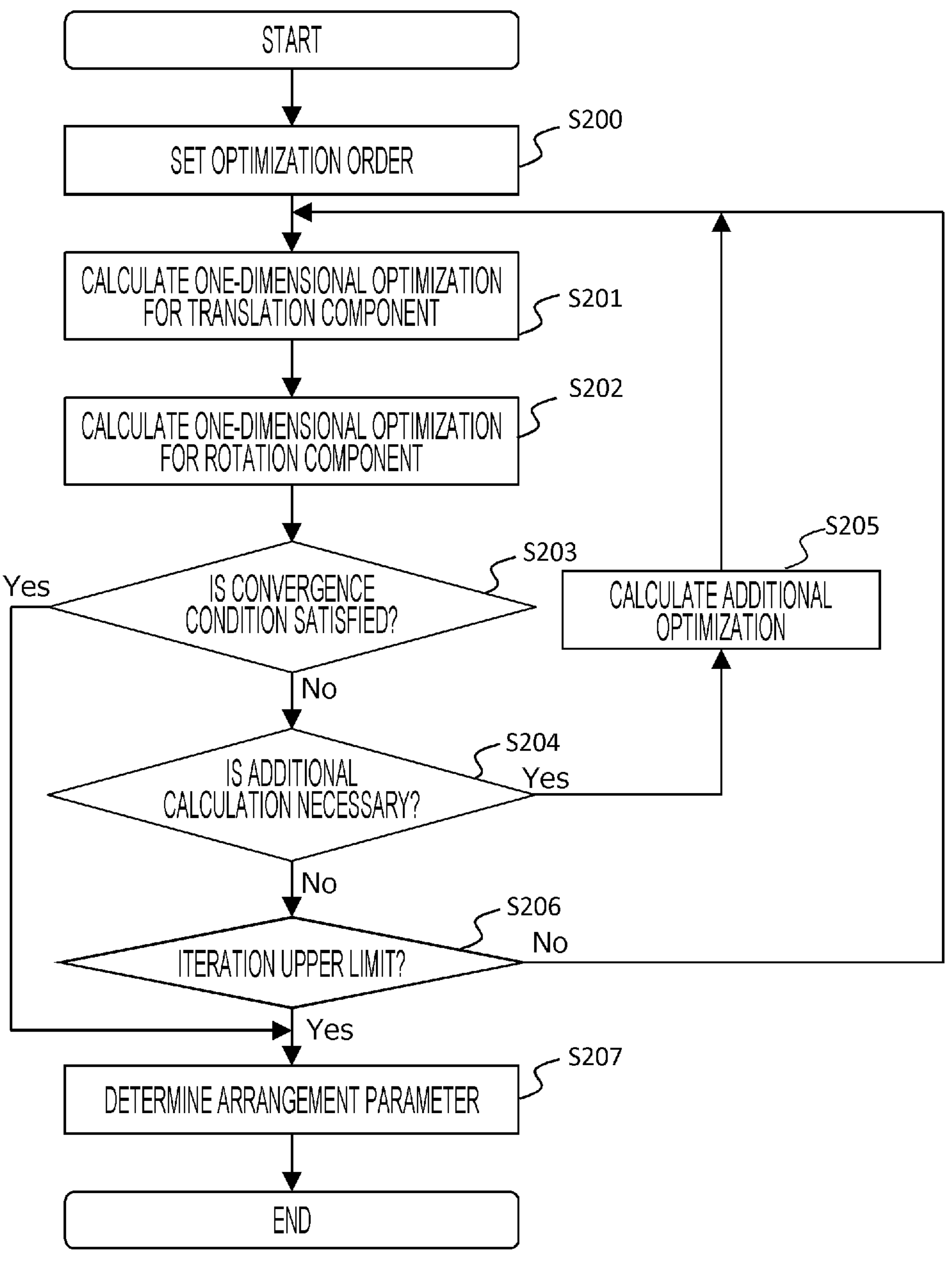
FIG. 3 is a flowchart for explaining optimization calculation processing in more detail.

FIG. 3 is a flowchart for explaining the optimization calculation processing, which is the processing of Steps S102 to 106 of FIG. 2, in more detail.

In the optimization calculation processing, the optimization calculation processing unit 25 sets an optimization order in which optimization is performed for the six components of the arrangement parameters (Step S200). Here, the optimization calculation processing unit 25 sets the optimization order to the order of three components related to the translation amount and three components related to the rotation amount. Hereinafter, the component related to the translation amount may be referred to as a translation parameter, and the component related to the rotation amount may be referred to as a rotation parameter. In FIG. 2, the processing in Step S200 is omitted. In addition, in FIG. 3, processing (for example, the processing of Step S103 and S104) performed by a unit other than the optimization calculation processing unit 25 is omitted.

The optimization calculation processing unit 25 performs one-dimensional optimization calculation of optimizing the value of the translation parameter in order for each of the three components of the translation parameter according to the optimization order (Step S201). The one-dimensional optimization calculation is processing of calculating a value of a parameter in which the similarity between the X-ray fluoroscopic image information and the simulated-X-ray fluoroscopic image information in the ROI is the largest in the one-dimensional direction along the optimum axis to be optimized by using a known Brent method or the like.

Figure 4:
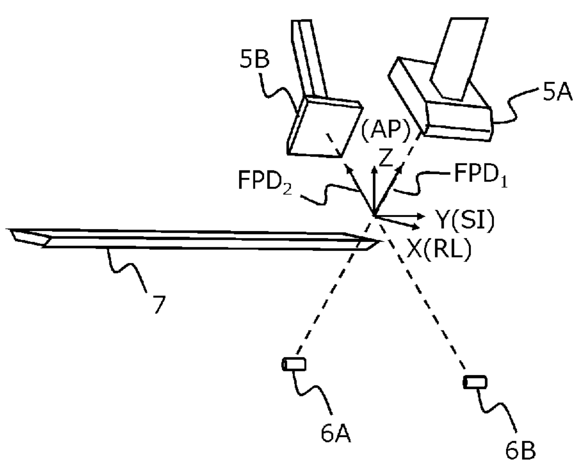
FIG. 4 is a diagram illustrating an example of an optimization axis of a translation parameter.

FIG. 4 is a diagram illustrating an example of an optimization axis of a translation parameter. In the example of FIG. 4, the movement axis along which the treatment couch 7 translates is an x(RL) axis, a y(SI) axis, and a z(AP) axis. The optimization axes of the translation parameter are an $FPD_1$ axis which is an imaging axis connecting the center of the FPD 5A and the X-ray tube 6A, an $FPD_2$ axis which is an imaging axis connecting the center of the FPD 5B and the X-ray tube 6B, and a y axis.

In a case where the $FPD_1$ axis and the $FPD_2$ axis are different from the x axis and the z axis as in the present embodiment (in the example of FIG. 4, arranged to be inclined by 45 degrees), when the x axis and the z axis are set as optimization axes, there is a possibility that an optimization difficult event that is difficult to optimize occurs. Meanwhile, in the present embodiment, it is possible to suppress the optimization difficult event by setting the optimization axes of the translation parameters to the $FPD_1$ axis, the $FPD_2$ axis, and the y axis without performing the optimization calculation of the two translation directions with the x axis and the z axis as the optimization axes. The optimization difficult event is an event in which the result of performing the optimization calculation in the one-dimensional direction affects the result of the optimization calculation in another direction, the number of iterations of the optimization calculation increases, or the optimum value cannot be reached due to the influence of the local optimal solution.

Figure 5:
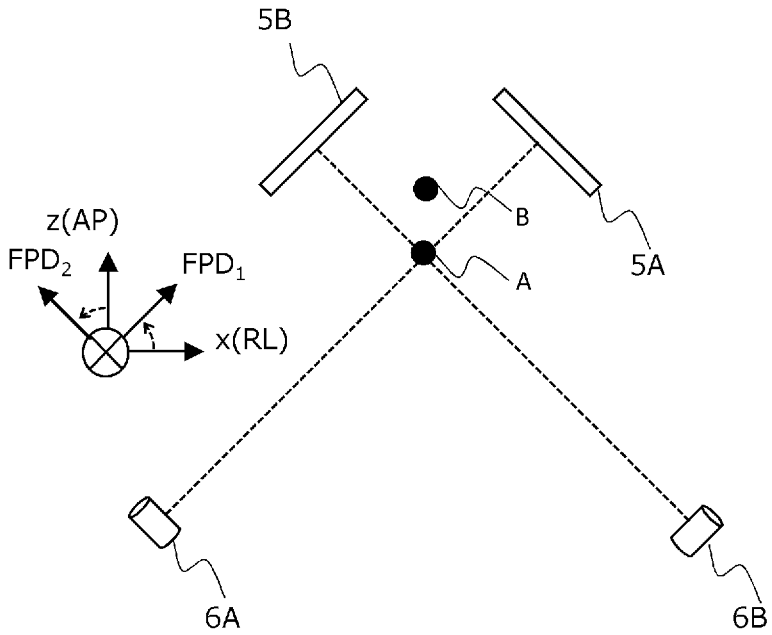
FIG. 5 is a diagram illustrating an example of a relationship between the optimization axis and an imaging system.
Figure 6:
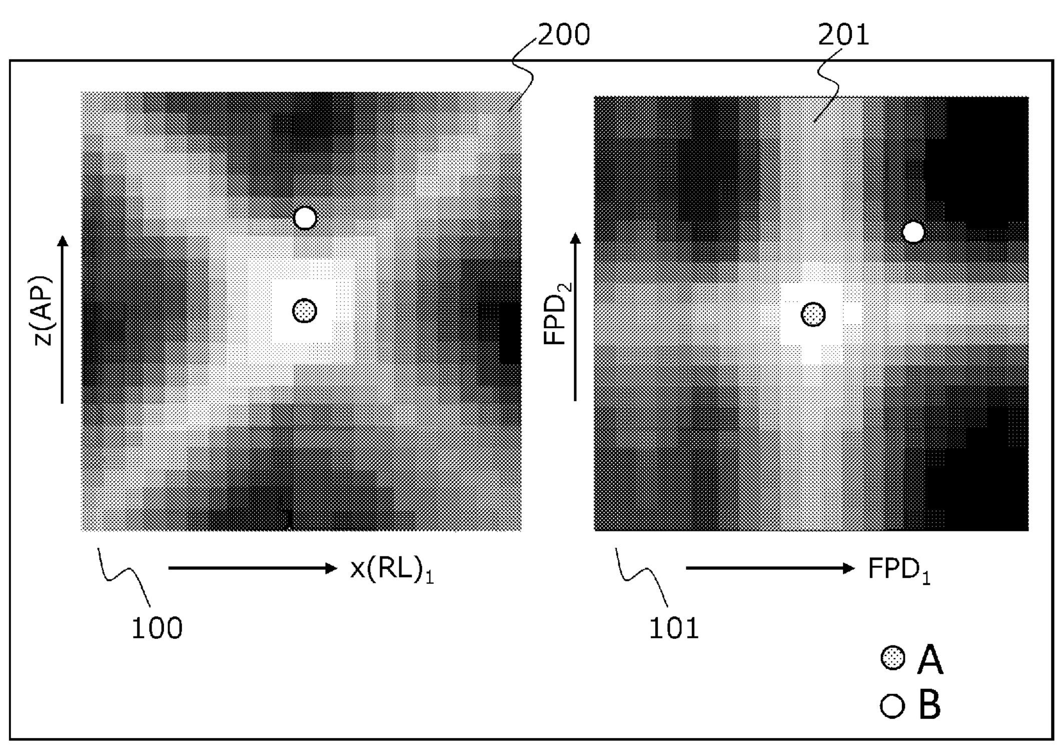
FIG. 6 is a diagram illustrating an example of a score map image.

FIGS. 5 and 6 are diagrams for explaining the optimization difficulty phenomenon in more detail.

FIG. 5 is a diagram illustrating a relationship between an optimization axis and an imaging system (FPDs 5A and 5B and X-ray tubes 6A and 6B). In the example of FIG. 5, the $FPD_1$ axis and the $FPD_2$ axis are oriented along a plane orthogonal to the y axis (a plane formed by the x axis and the z axis), and are shifted from the x axis and the z axis by 45 degrees, respectively.

FIG. 6 is a diagram illustrating a score map image representing a distribution of matching scores as the similarity between the X-ray fluoroscopic image and the simulated-X-ray fluoroscopic image. Specifically, the score map image is an image indicating a matching score for each relative position with respect to the position on the planned arrangement of the positioning target structure. Shading of the score map image represents a magnitude of the matching score, and the brighter the shading, the higher the matching score.

A score map image 100 illustrated in FIG. 6(*a*) represents the distribution of the matching scores in the x-axis direction and the z-axis direction in a case where the optimization axis is the movement axis (x-axis, y-axis, and z-axis) of the treatment couch 7, and a score map image 101 illustrated in FIG. 6(*b*) represents the distribution in the $FPD_1$ axis direction and the $FPD_2$ axis direction in a case where the optimization axis is the $FPD_1$ axis, the $FPD_2$ axis, and the y-axis as in the present embodiment.

In the case of FIG. 6(*a*), in the score map image 100, a high score band 200 having a high matching score exists in an oblique direction. This is because the high score band 200 appears along the imaging axes (the $FPD_1$ axis and the $FPD_2$ axis).

At this time, in a case where the positioning target structure exists at the position B when the position of the positioning target structure in the treatment planning is the position A, the matching score is a value corresponding to the position B in the score map image 100. In the one-dimensional optimization calculation, the value of the parameter is determined such that the matching score is the highest in the one-dimensional direction along the target optimization axis. For example, when the optimization calculation in the y-axis direction and the z-axis direction is performed after the optimization calculation in the x-axis direction, the position of the positioning target structure in the score map image 100 does not immediately become the position A, but is optimized to the position of the high score band 200 existing on the x-direction side of the position B. Thereafter, by repeating the optimization calculation, the position of the positioning target structure in the score map image 100 is updated in zigzag and the values in the x direction and the z direction in the high score band 200. As a result, the number of iterations of the optimization calculation increases, and in some cases, the value of the parameter is locally optimized, and an appropriate value may not be reached.

Meanwhile, in the score map image 101 in a case where the optimization axes are the $FPD_1$ axis and the $FPD_2$ axis as the imaging axes as in the present embodiment, the high score band 201 exists along the optimization axis. Therefore, it is possible to suppress the zigzag update of the position of the positioning target structure in the score map image 100 as described above, and the value of the parameter can be efficiently optimized to an appropriate value.

The description returns to FIG. 3. When Step S201 ends, the optimization calculation processing unit 25 performs one-dimensional optimization calculation for each component of the rotation component (Step S202). In the optimization calculation of the rotation component, the optimization axis (rotation axis) may be the same as the movement axis (x, y, z) of the treatment couch 7, or may be the same as the optimization axis (FPD1 axis, FPD2 axis, y axis) of the translation component.

The optimization calculation processing unit 25 determines whether or not an optimization result that is a result of the optimization calculation of the arrangement parameters satisfies a convergence condition (Step S203).

For example, in a case where the Powell method is used as the optimization calculation method, the optimization calculation processing unit 25 determines that the optimization result satisfies the convergence condition when Formula (2) is satisfied in a case where the matching score (similarity) in the current optimization result is $f_{ret}$ and the matching score in the previous optimization result is $f_p$.

[Mathematical Formula 2]

$$|f_p - f_{ret}| \leq r \times \frac{|f_p + f_{ret}|}{2} \tag{2}$$

Here, r is a constant value called a relative allowable error value, and may be determined in advance or may be settable by the user, for example. Note that $|f_p - f_{ret}|$ represents a change amount of the matching score in the current optimization result from the matching score in the previous optimization result, and $(|f_p|+|f_{ret}|)/2$ represents an average value of the matching score in the current optimization result and the matching score in the previous optimization result.

When the convergence condition is not satisfied (Step S203: No), the optimization calculation processing unit 25 determines whether or not an additional optimization calculation process is necessary (Step S204).

For example, in a case where the Powell method is used as the optimization calculation method, the optimization calculation processing unit 25 determines whether or not additional optimization calculation is necessary, using three functions $f_0$, $f_N$, and $f_E$ expressed by Formula (3).

[Mathematical Formula 3]

$$\begin{aligned} f_0 &= f(P_0) \\ f_N &= f(P_N) \\ f_E &= f(2P_N - P_0) \end{aligned} \tag{3}$$

The function $f_0$ indicates the matching score at a start point $P_0$ before the current optimization calculation, and the function $f_N$ indicates the matching point at the optimization point $P_N$ after the current optimization calculation. In addition, the function $f_E$ indicates a matching point at a point advanced from the optimization point $P_N$ by the same distance as the distance from the start point $P_0$ to the optimization point $P_N$ in an average movement direction which is the direction from the start point $P_0$ to the optimization point $P_N$. Note that the start point $P_0$ and the optimization point $P_N$ represent points (positions) in the score map image 100 of the positioning target structure.

In a case where at least one of the following Formulas (4) and (5) regarding the functions $f_0$, $f_N$, and $f_E$ is applicable, the optimization calculation processing unit 25 determines that there is no need to perform additional optimization calculation.

[Mathematical Formula 4]

$$f_E \geq f_0 \tag{4}$$

$$2(f_0 - 2f_N + f_E)[(f_0 - f_N) - \Delta f]^2 \geq (f_0 - f_E)^2 \Delta f \tag{5}$$

Here, $\Delta f$ is an absolute value of a value having the largest change amount among the decrease amounts of the matching score along each direction of the optimization axis in the current optimization calculation.

In a case where the Formula (4) is satisfied, it indicates that the decrease amount of the matching score along the average movement direction depends only on the component in one direction. In addition, in a case where Formula (5) is satisfied, it indicates that the value of the matching score is already a local optimal solution.

In a case where additional optimization calculation is required (Step S204: Yes), the optimization calculation processing unit 25 performs additional optimization calculation (Step S205), and returns to the processing of Step S201. The additional optimization calculation is a one-dimensional optimization calculation with respect to the average movement direction from the start point $P_0$ toward the optimization point $P_N$.

When the additional optimization calculation processing is unnecessary (Step S204: No), the optimization calculation processing unit 25 determines whether or not the number of iterations of the optimization calculation (the number of times the optimization processing including the processing of Step S201 and S202 has been executed) has reached an upper limit number specified in advance (Step S206).

When the number of repetitions has not reached the upper limit value (Step S206: No), the processing of Step S201 is executed again.

In addition, in a case where the convergence condition is satisfied (Step S203: Yes) and in a case where the number of repetitions has reached the upper limit value (Step S206: Yes), the optimization calculation processing unit 25 determines the value of the arrangement parameter to be the optimized value (Step S207), and proceeds to Step S107 of FIG. 2.

In the present embodiment, the particle beam therapy system is exemplified as the radiotherapy device, but the radiotherapy device is not limited to the particle beam therapy system, and may be a radiotherapy system using a non-particle beam such as an X-ray. In this case, the accelerator 1 includes, for example, an electron beam accelerator that outputs X-rays.

As described above, in the present embodiment, the image acquisition unit 21 acquires the plurality of X-ray fluoroscopic images obtained by imaging the patient B along each of the plurality of imaging axes in directions different from the plurality of movement axes along which the treatment couch 7 on which the patient B is mounted translates. The simulated-X-ray fluoroscopic image creation unit 22 creates the plurality of simulated-X-ray fluoroscopic images obtained by projecting the three-dimensional fluoroscopic image of the patient B on each of the plurality of surfaces corresponding to each imaging axis. The similarity calculation unit 24 calculates the similarity between each X-ray fluoroscopic image and each simulated-X-ray fluoroscopic image. Based on the similarity, the optimization calculation processing unit 25 calculates the movement amount of the treatment couch 7 such that each X-ray fluoroscopic image and each simulated-X-ray fluoroscopic image coincide most in each of the plurality of translation directions along each of the plurality of optimization axes including the plurality of imaging axes and the plurality of rotation directions around the plurality of rotation axes.

Therefore, since the optimization calculation is performed in the directions along the plurality of imaging axes, it is possible to reduce the event that the optimum value of the parameter cannot be reached or the number of calculations increases. Therefore, it is possible to perform highly accurate patient positioning while further reducing the calculation time.

In the present embodiment, the imaging axes are substantially orthogonal to each other. Therefore, the parameter can be more appropriately optimized.

In the present embodiment, the number of imaging axes is two. Therefore, since the optimization calculation can be performed in the minimum necessary direction, an increase in the calculation amount can be suppressed.

Further, in the present embodiment, the imaging axis is oriented in a direction along a plane formed by any two axes of the movement axes. Therefore, the optimization calculation can be more appropriately performed.

In addition, in the present embodiment, since the rotation axis is the same as the optimization axis, the optimization calculation can be more appropriately performed.

In addition, in the present embodiment, since the movement amount of the treatment couch 7 is calculated so that the regions in the ROI coincide most, the optimization calculation can be more appropriately performed.

The above-described embodiments of the present disclosure are examples for describing the present disclosure, and are not intended to limit the scope of the present disclosure only to those embodiments. Those skilled in the art can practice the present disclosure in various other aspects without departing from the scope of the present disclosure.

REFERENCE SIGNS LIST

A particle beam therapy system
B patient
1 accelerator
2 beam transport device
3 gantry
4 irradiation nozzle
5A FPD
5B FPD
6A X-ray tube
6B X-ray tube
7 treatment couch
8 robot arm
9 communication device patient
10 data server
11 treatment planning system
12 X-ray fluoroscopic imaging device
13 treatment-couch control system
20 patient positioning device
21 simulated-X-ray fluoroscopic image creation unit
22 ROI drawing unit
23 similarity calculation unit
24 optimization calculation processing unit
25 image display unit
26 control unit

The invention claimed is:

1. A positioning device that controls a position of a treatment couch on which a subject is mounted, the positioning device comprising:

an image acquisition unit that acquires a plurality of fluoroscopic images obtained by imaging the subject along each of a plurality of imaging axes in a direction different from a plurality of movement axes along which the treatment couch translationally moves;

a creation unit that creates a plurality of simulated fluoroscopic images obtained by projecting a three-dimensional fluoroscopic image of the subject onto each of a plurality of surfaces corresponding to each imaging axis of the plurality of imaging axes;

a calculation unit that calculates a similarity between each of the plurality of fluoroscopic images and each of the plurality of simulated fluoroscopic images; and an optimization unit that calculates, based on the similarity, a movement amount of the treatment couch such that each fluoroscopic image and each simulated fluoroscopic image match most in each of a plurality of translation directions along each of a plurality of optimization axes including the plurality of imaging axes and a plurality of rotation directions around a plurality of rotation axes, wherein each rotation axis of the plurality of rotation axes is identical to an optimization axis of the plurality of optimization axes.

2. The positioning device according to claim 1, wherein the plurality of imaging axes is substantially orthogonal to each other.

3. The positioning device according to claim 1, wherein a number of the plurality of imaging axes is two.

4. The positioning device according to claim 3, wherein a number of the plurality of movement axes is two or more, and each imaging axis of the plurality of imaging axes is oriented in a direction along a plane formed by any two of the plurality of movement axes.

5. The positioning device according to claim 1, wherein the optimization unit further calculates the movement amount of the treatment couch such that a region of interest set on each simulated fluoroscopic image and a region on each fluoroscopic image corresponding to the region of interest match most.

6. A radiotherapy device comprising:

the positioning device according to claim 1;

a treatment-couch control system that moves the treatment couch based on the movement amount calculated by the optimization unit; and an irradiation device that irradiates the subject mounted on the moved treatment couch with radiation.

7. A positioning method using a positioning device that controls a position of a treatment couch on which a subject is mounted, the positioning method comprising:

acquiring a plurality of fluoroscopic images obtained by imaging the subject along each of a plurality of imaging axes in a direction different from a plurality of movement axes along which the treatment couch translationally moves;

creating a plurality of simulated fluoroscopic images obtained by projecting a three-dimensional fluoroscopic image of the subject onto each of a plurality of surfaces corresponding to each imaging axis of the plurality of imaging axes;

calculating a similarity between each fluoroscopic image and each simulated fluoroscopic image; and calculating, based on the similarity, a movement amount of the treatment couch such that each fluoroscopic image and each simulated fluoroscopic image coincide most in each of a plurality of translation directions along each of a plurality of optimization axes including the plurality of imaging axes and a plurality of rotation directions around a plurality of rotation axes, wherein each rotation axis of the plurality of rotation axes is identical to an optimization axis of the plurality of optimization axes.

* * * * *